(12) United States Patent
Shin et al.

(10) Patent No.: US 8,525,992 B2
(45) Date of Patent: Sep. 3, 2013

(54) METHOD AND APPARATUS OF MEASURING RELATIVE PHASE OF BIO-CELLS

(75) Inventors: In Hee Shin, Gwangji (KR); Sang Mo Shin, Gwangju (KR)

(73) Assignee: Gwangju Institute of Science and Technology, Gwangju (JP)

( * ) Notice: Subject to any disclaimer, the term of this patent is extended or adjusted under 35 U.S.C. 154(b) by 320 days.

(21) Appl. No.: 12/900,420

(22) Filed: Oct. 7, 2010

(65) Prior Publication Data

US 2011/0085163 A1    Apr. 14, 2011

(30) Foreign Application Priority Data

Oct. 8, 2009    (KR) .................. 10-2009-0095848

(51) Int. Cl.
*G01J 4/00*    (2006.01)
(52) U.S. Cl.
USPC ........................................... 356/367

(58) Field of Classification Search
USPC .................. 356/364, 368, 322, 327
See application file for complete search history.

(56) References Cited

U.S. PATENT DOCUMENTS

2005/0122514 A1* 6/2005 Jang ............................. 356/365
2010/0103417 A1* 4/2010 Otani et al. ................... 356/364

* cited by examiner

*Primary Examiner* — Kara E Geisel
(74) *Attorney, Agent, or Firm* — Stein IP, LLC

(57) ABSTRACT

A method of measuring a relative phase of a bio-cell using a digital image sensor, comprising the steps of firstly filtering a light emitted from a light source, using a first polarizer and a first wave plate, which are arranged in order in a optical path, exposing a bio-cell to the firstly filtered light, secondly filtering the light passing through the bio-cell, using a second wave plate and a second polarizer, which are arranged in order in the optical path, and sensing an intensity of the secondly filtered light, by each of pixels of the image sensor, wherein, as conditions of the second filtering are varied, optical properties of the bio-cell are calculated using the intensity of the light in a pixel-wise manner.

8 Claims, 1 Drawing Sheet

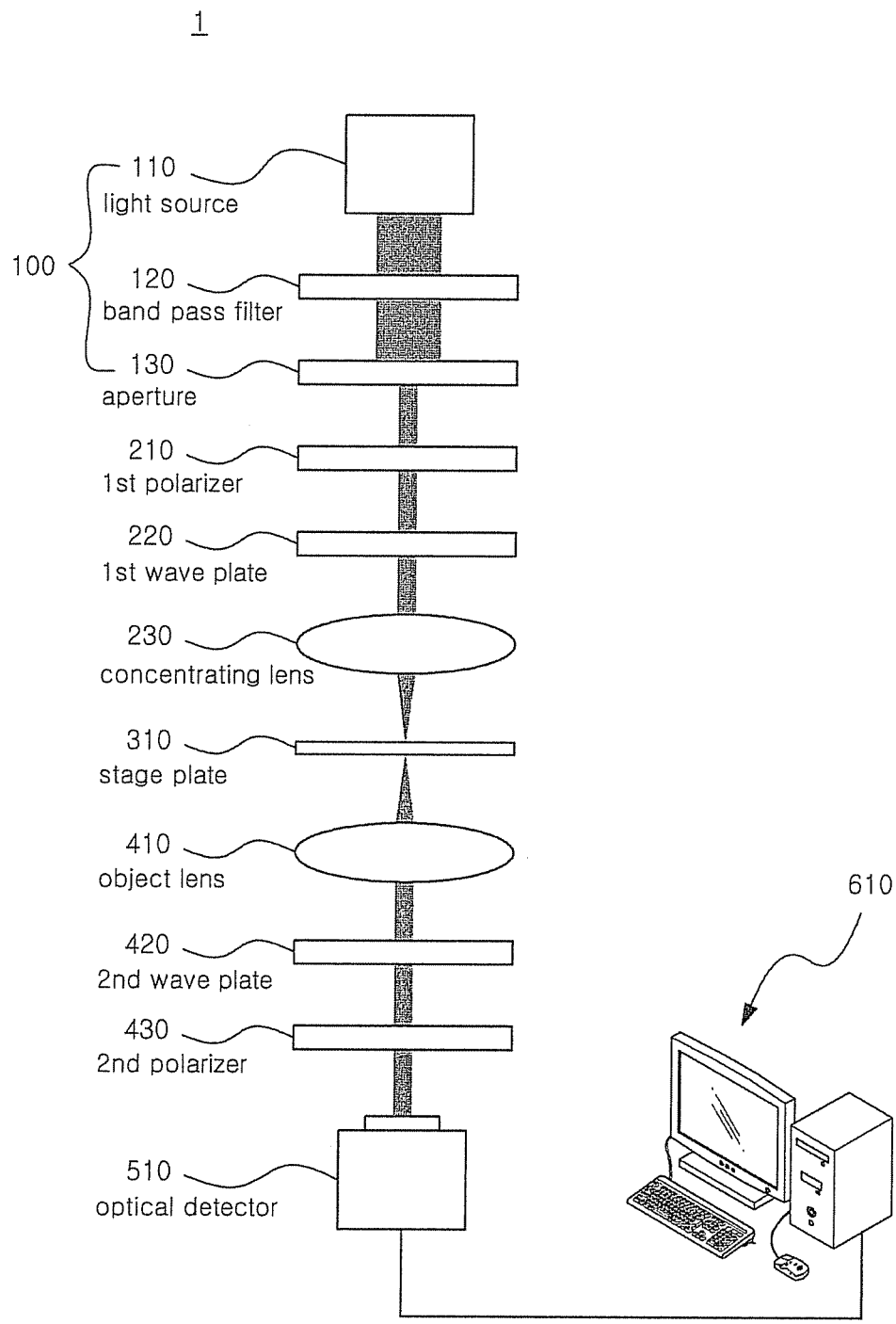

METHOD AND APPARATUS OF MEASURING RELATIVE PHASE OF BIO-CELLS

CROSS-REFERENCE TO RELATED APPLICATION

This application claims the benefit of Korean Patent Application No. 10-2009-0095848, filed on Oct. 8, 2009, in the Korean Intellectual Property Office, the disclosure of which is incorporated herein by reference.

BACKGROUND OF THE INVENTION

1. Technical Field

The present invention relates to a method and an apparatus of measuring a relative phase of a bio-cell or bio-cells, more particularly, relates to a method and an apparatus of measuring a relative phase of a bio-cell, for making an image of the bio-cell by measuring its polarization state and relative phases.

2. Background Art

As observing bio-cells in real time conventionally is getting important in view of mobility, drug reaction, division property and the like of the bio-cells, researches for the real-time observation without pre-processing are ongoing, instead of performing an irreversible bio-chemical process like dyeing. Namely, in these days, the technologies of cell detection that are enable observing and re-measuring cells without destructive process attract great attention.

To observe cell tissue as a specimen without destruction, an optical microscope may be used for the observation of biological sample, such as bio-cell. However, since many of the bio-cells are substantially invisible with the naked eye, it is difficult to observe the bio-cells in that any absorption of the light does not occur.

Accordingly, conventionally developed are a phase-contrast microscope and a DIC microscope, in order to observe the bio-cells in visible area.

At first, the phase contrast microscope is a microscope that uses the difference of the refractive index, unlike the usual optical microscope, to display the difference of the contrast using the interference between the diffracted ray and not-diffracted ray.

Otherwise, the DIC microscope is a microscope that uses the natural phenomenon that the light speed is decreased in a material to display the interference between a light passing through a sample and a light well-separated from a light source.

The above mentioned phase contrast microscope and interference microscope make it possible to observe the biological sample, like a bio-cell, that is invisible through the conventional optical microscope, however, since they just provide qualitative phase information, the precise interpretation to the biological sample easily reaches the limit. Thus, it is necessary to develop apparatuses or devices that can provide quantitative phase information about the biological sample.

To develop microscopy technology, a method of imaging quantitative phase information of the biological sample is being studied. For example, an imaging device that measures the bio-cell's phase and birefringence using OCT (Optical Coherent Tomography) to calculate the quantitative phase information and make an image of inside of the sample, is developed, however, in spite of its slow detection speed, it needs a high-speed scanning device, has a difficulty to observe the bio-cell in real time, and produces a noisy sound.

SUMMARY OF THE INVENTION

The present invention provides a method and an apparatus of measuring a relative phase of a bio cell that can help to observe the bio cell in real time without pre-processing like dyeing and fixation.

The present invention provides a method and an apparatus of measuring a relative phase of a bio cell that can identify a bio cell that is composed of multilayer in real time.

According to one exemplary embodiment of this invention, a method of measuring a relative phase of a bio cell using a digital image sensor, comprises the steps of firstly filtering a light emitted from a light source, using a first polarizer and a first wave plate, which are arranged in order in a optical path, exposing a bio-cell to the firstly filter light, secondly filtering the light passing through the bio-cell, using a second wave plate and a second polarizer, which are arranged in order in the optical path, and sensing an intensity of the secondly filter light, by each of pixels of the image sensor, wherein, as conditions of the second filtering are varied, optical properties of the bio-cell are calculated using the intensity of the light in a pixel-wise manner.

The optical properties of the bio cell may refer to an amount of the phase delay of light delayed by the bio cell, and, for example the intensities of the light filtered in the first and second filtering, may be measured by an optical detector like a CCD camera (charge-coupled device camera) in a pixel-wise manner. In this case, the filtering conditions may be varied during the second filtering, the intensities of the light may be detected under different filtering conditions respectively, and the optical properties, such as phase delay, may be calculated using the intensities of the light.

In this instance, the optical properties affected by the varied conditions may be converted into electric signals in the optical detector, may be transferred to a central processing unit. The central processing unit may calculate the phase delay of the light using the detected properties, so as to make an image of the bio cell.

When the first wave plate and the second wave plate are provided by using quarter-wave length plate and positioned at 45° and 135° respectively to a polarization axis defined by the first polarizer, the optical properties, such as intensities of the light passing through the second polarizer, calculated in a pixel-wise manner may be represented in a Jones matrix, as follows:

$$\begin{bmatrix} E_x \\ E_y \end{bmatrix} = \begin{bmatrix} \cos\beta & -\sin\beta \\ \sin\beta & \cos\beta \end{bmatrix} \begin{bmatrix} 1 & 0 \\ 0 & 0 \end{bmatrix} \begin{bmatrix} \cos\beta & \sin\beta \\ -\sin\beta & \cos\beta \end{bmatrix} \begin{bmatrix} \cos(135°) & -\sin(135°) \\ \sin(135°) & \cos(135°) \end{bmatrix}$$

$$\begin{bmatrix} e^{i\frac{\pi}{4}} & 0 \\ 0 & e^{-i\frac{\pi}{4}} \end{bmatrix} \begin{bmatrix} \cos(135°) & \sin(135°) \\ -\sin(135°) & \cos(135°) \end{bmatrix} \times \begin{bmatrix} e^{i\frac{\delta}{2}} & 0 \\ 0 & e^{-i\frac{\delta}{2}} \end{bmatrix} \begin{bmatrix} \cos 45 & -\sin 45 \\ \sin 45 & \cos 45 \end{bmatrix}$$

$$\begin{bmatrix} e^{i\frac{\pi}{4}} & 0 \\ 0 & e^{-i\frac{\pi}{4}} \end{bmatrix} \begin{bmatrix} \cos 45 & \sin 45 \\ -\sin 45 & \cos 45 \end{bmatrix} \begin{bmatrix} 0 \\ 1 \end{bmatrix} E_0 e^{i\omega t}$$

Whereby $E_x$ and $E_y$ are intensities of the light respectively to x axis and y axis, $\beta$ is a rotating angle of the second polarizer, $\delta$ is a phase delay by the bio-cell, $E_0$ is an amplitude of an initial light, and $\omega$ is a frequency of the initial light.

Rotating the second polarizer by $\pi/4$ in 4 times, 4 set of light intensities may be obtained by substituting the angle to $\beta$. In this case, an equation of $\delta = \arctan\{(I_3-I_1)/(I_2-I_4)\}$ may be induced, and the phase delay $\delta$ of the bio cell may be calculated using the equation.

Since the phase delay of the bio cell is calculated using 4 light intensities due to the rotation of the second polarizer, it is possible to make an image of the bio cell without an additional pre-processing. Moreover, comparing to the conventional device to make an image of bio cells using OCT (Optical Coherent Tomography), the apparatus of this invention is very fast to enable the researcher to observe bio cells in real time.

According to another exemplary embodiment of this invention, an apparatus of measuring a relative phase of a bio-cell, comprises a light source member having a light source emitting light, a first polarizer for polarizing the light from the light source to a specific direction of polarization state, a first wave plate for affecting the polarization direction of the light passing through the first polarizer, a stage plate for locating the bio-cell on an optical path of the light passing through the first wave plate, a second wave plate for affecting the polarization direction of the light passing though the stage plate, a second polarizer for polarizing the light passing through the second wave plate to another specific direction of polarization state, and an image reading member having an image sensor detecting intensities of the light passing through the second polarizer.

The apparatus of this invention can detect intensities passing through a bio cell to make an image using the results. Since pre-processing like dyeing is not necessary, researcher can observe the changes or reactions of the bio cell under a natural condition.

The apparatus and method of this invention calculate a relative phase of the bio cell using 4 images obtained through changes of the polarization states of polarizer, such that they can make an image of multilayer bio cell very quickly and help to observe the changes of the bio cell in real time.

Since the apparatus of this invention obtain an image of a bio cell simply through changing the polarization states of the polarizer, the system for this invention may be simple and cheaply constructed.

DESCRIPTION OF THE DRAWINGS

The above and/or other aspects and advantages of the present invention will become apparent and more readily appreciated from the following detailed description, taken in conjunction with the accompanying drawings of which:

FIG. 1 is a schematic view illustrating an apparatus of measuring a relative phase of a bio cell according to one embodiment of this invention.

DETAILED DESCRIPTION OF THE EMBODIMENTS

Reference will now be made in detail to embodiments of the present invention, examples of which are illustrated in the accompanying drawings, wherein like reference numerals refer to the like elements throughout. The embodiments are described below in order to explain the present invention by referring to figures.

A method of measuring a relative phase of a bio cell according to one embodiment of this invention, comprises firstly filtering a light emitted from a light source, using a first polarizer and a first wave plate, which are arranged in order in a optical path, exposing a bio-cell to the firstly filter light, secondly filtering the light passing through the bio-cell, using a second wave plate and a second polarizer, which are arranged in order in the optical path, and sensing an intensity of the secondly filter light, by each of pixels of the image sensor, wherein, as conditions of the second filtering are varied, optical properties of the bio-cell are calculated using the intensity of the light in a pixel-wise manner.

In this case, the optical properties of the bio cell may refer to an amount of the phase delay of light delayed by the bio cell, and, for example the intensities of the light filtered in the first and second filtering, may be measured by an optical detector like a CCD camera (charge-coupled device camera) or CMOS image sensor, in a pixel-wise manner. The filtering conditions may be varied during the second filtering, the intensities of the light may be detected under different filtering conditions respectively, and the optical properties, such as phase delay, may be calculated using the intensities of the light.

The optical properties affected by the varied conditions may be converted into electric signals in the optical detector, may be transferred to a central processing unit. The central processing unit may calculate the phase delay of the light using the detected properties, so as to make an image of the bio cell.

The above method of measuring the relative phase of the bio cell may be performed through the following apparatus as below; hereinafter an apparatus for measuring a relative phase is described in detail.

FIG. 1 is a schematic view illustrating an apparatus of measuring a relative phase of a bio cell according to one embodiment of this invention.

Referring to FIG. 1, an apparatus 1 according to this embodiment comprises a light source member 100, a first polarizer 210, a first wave plate 220, a stage plate 310, a second wave plate 420, a second polarizer 430 and a phase image generator 610.

The light source member 100 comprises a light source 110 emitting light, a band pass filter 120 selectively passing a specific wavelength of light selected from the incident light emitted from the light source 110, an aperture 130 controlling the amount of the light, in which the light source 110, the band pass filter 120 and the aperture 130 are arranged downwardly in order.

The band pass filter 120 may be chosen in accordance with specific wavelength properties of the polarizer and wave plate, because the polarizer and the wave plate used in the first and second filtering may have different polarization property depending on the wavelength of the used light.

As mentioned above, the light emitted from the light source member 100 is firstly filtered and the first filtering is performed by the first polarizer 210 and the first wave plate 220 located on an optical path in order.

Then, the firstly filtered light may be concentrated by the concentrating lens 230 to go to the bio cell. The bio cell is set on the stage plate 310 which is located on the optical path.

For reference, the polarizer in this specification may refer to an optical element to change not-polarized electro-magnetic wave (for example light) to a desired single polarization state (linear polarization state). The wave plate may refer to an optical element to change a polarizing direction of the light passing through itself. The polarization direction of the light passing through the wave plate may be a vector sum of elements parallel or vertical to the optical path and the vector sum of two elements may be changed according to the birefringence index and thickness of the wave plate, such that the polarization direction of the light may be changed. Namely, the changes of the phase of the light passing through the wave plate may occur. The first and second wave plates according to this embodiment may be a quarter-wave length plate which could change its polarization direction by 90°.

In this instance, the stage plate 310 is able to move horizontally and vertically, in order to position the bio cell in the focus of a condensing lens 230.

The light passing through the stage plate 310 is secondly filtered again, which can be performed by the second wave plate 420 and the second polarizer 430 located on the optical path in order.

On the other hand, the light passing through the stage plate 310 may go through an object lens 410 before the second wave plate 420.

As mentioned above, the light emitted from the light source member 100 goes through the first and second filterings to an optical detector 510, such as a CCD camera or CMOS image sensor which can measure the intensity of light.

Then the intensity of the light measured in the optical detector 510 may be converted into electric signals to be transferred to the phase image generator 610, for example a computer, which comprises a central processing unit, a display and the like, and the central processing unit may calculate the phase delay of the light using the detected intensities. The calculated phase delay may be used in order to make an image of the bio cell.

The intensities of the light passing through the first and second filterings may be measured in the optical detector 510 in a pixel-wise manner. As the conditions of the filtering are changed, especially at the second filtering, the intensities detected under the changed filtering conditions may be used to calculate phase delays of the light.

When secondly filtering the light, the polarization angle of the second polarizer 430 may be changed. In this case, a linear polarizer may be used as the second polarizer 430 to vary the polarization state. In case that the second polarizer comprises a polarizing rotator having a liquid-crystal phase delayer, the polarization state may be varied according to the liquid-crystal state of the liquid-crystal phase delayer.

The linear polarizer rotated by the force of a stepping motor has a high degree of accuracy, but may need a relatively long detection time to rotate itself with the stepping motor. However, since the liquid-crystal phase delayer controls the liquid crystal state with electric signal, it has a very short detection time.

Hereinafter, described in detail the method of calculate the relative phase delayed by the bio cell using the intensities of the light experienced the first and second filterings.

At first, as shown in FIG. 1, the first polarizer 210, the first wave plate 220, the second wave plate 420 and the second polarizer 430 are arranged on the optical path in order. If the relative phase of the bio cell is determined on the x, y axis of FIG. 1, the phase difference may refer to a reference number δ to be substituted in the following matrix equation, e.g. Jones matrix, to find out the polarization state affected by the polarization element and the bio cell.

$$\begin{bmatrix} E_x \\ E_y \end{bmatrix} = \begin{bmatrix} \cos\beta & -\sin\beta \\ \sin\beta & \cos\beta \end{bmatrix} \begin{bmatrix} 1 & 0 \\ 0 & 0 \end{bmatrix} \begin{bmatrix} \cos\beta & \sin\beta \\ -\sin\beta & \cos\beta \end{bmatrix}$$ [Equation 1]

$$\begin{bmatrix} \cos(135°) & -\sin(135°) \\ \sin(135°) & \cos(135°) \end{bmatrix} \begin{bmatrix} e^{i\frac{\pi}{4}} & 0 \\ 0 & e^{-i\frac{\pi}{4}} \end{bmatrix}$$

$$\begin{bmatrix} \cos(135°) & \sin(135°) \\ -\sin(135°) & \cos(135°) \end{bmatrix} \times$$

$$\begin{bmatrix} e^{i\frac{\delta}{2}} & 0 \\ 0 & e^{-i\frac{\delta}{2}} \end{bmatrix} \begin{bmatrix} \cos 45 & -\sin 45 \\ \sin 45 & \cos 45 \end{bmatrix}$$

$$\begin{bmatrix} e^{i\frac{\pi}{4}} & 0 \\ 0 & e^{-i\frac{\pi}{4}} \end{bmatrix} \begin{bmatrix} \cos 45 & \sin 45 \\ -\sin 45 & \cos 45 \end{bmatrix} \begin{bmatrix} 0 \\ 1 \end{bmatrix} E_0 e^{i\omega t}$$

In Equation 1, $E_x$ and $E_y$ are intensities of the light respectively to x axis and y axis, β is a rotating angle of the second polarizer, δ is a phase delay by the bio-cell, $E_0$ is an amplitude of an initial light, ω is a frequency of the initial light.

$E_0 e^{i\omega t}$ is a Jones matrix of the light emitted from the light source member 100, $$\begin{bmatrix} 0 \\ 1 \end{bmatrix}$$

is a Jones matrix representing the first polarizer 210, $$\begin{bmatrix} \cos 45 & -\sin 45 \\ \sin 45 & \cos 45 \end{bmatrix} \begin{bmatrix} e^{i\frac{\pi}{4}} & 0 \\ 0 & e^{-i\frac{\pi}{4}} \end{bmatrix} \begin{bmatrix} \cos 45 & \sin 45 \\ -\sin 45 & \cos 45 \end{bmatrix}$$

is a Jones matrix representing the first wave plate 220, $$\begin{bmatrix} e^{i\frac{\delta}{2}} & 0 \\ 0 & e^{-i\frac{\delta}{2}} \end{bmatrix}$$

is a Jones matrix representing the bio cell, $$\begin{bmatrix} \cos(135°) & -\sin(135°) \\ \sin(135°) & \cos(135°) \end{bmatrix} \begin{bmatrix} e^{i\frac{\pi}{4}} & 0 \\ 0 & e^{-i\frac{\pi}{4}} \end{bmatrix} \begin{bmatrix} \cos(135°) & \sin(135°) \\ -\sin(135°) & \cos(135°) \end{bmatrix}$$

is a Jones matrix representing the second wave plate 420, and $$\begin{bmatrix} \cos\beta & -\sin\beta \\ \sin\beta & \cos\beta \end{bmatrix} \begin{bmatrix} 1 & 0 \\ 0 & 0 \end{bmatrix} \begin{bmatrix} \cos\beta & \sin\beta \\ -\sin\beta & \cos\beta \end{bmatrix}$$

is a Jones matrix representing the first polarizer 430.

In this instance, the first wave plate 220 and the second wave plate 420 are quarter wavelength plate.

An equation regarding to the intensity of light, according to the Jones matrix of Equation 1, is as below, $$I = I_b + I_m (\sin\delta \sin 2\beta - \cos\delta \cos 2\beta)$$ [Equation 2]

According to Equation 2, the intensity of the light may refer to the equation of $I_b = I_0 + E_0^2/2$, $I_m = I_0 + E_0^2/2$. In case that the second polarizer is a linear polarizer, the linear polarizer may be positioned at every π/4. As mentioned above, when the linear polarizer rotates at every π/4, 4 equations may be obtained using Equation 2 as follows,

| No. | Rotating angle of Second polarizer (radian) | Equation for intensity |
|---|---|---|
| 1 | 0 | $I_1 = I_b - I_m \cos\delta$ |
| 2 | $\pi/4$ | $I_2 = I_b + I_m \sin\delta$ |
| 3 | $\pi/2$ | $I_3 = I_b + I_m \cos\delta$ |
| 4 | $3\pi/4$ | $I_4 = I_b - I_m \sin\delta$ |

Using the above 4 equations regarding to the intensity of the light, the phase delay of the bio cell may be calculated using the below Equation 3.

$$\delta = \arctan\{(I_3 - I_1)/(I_2 - I_4)\} \quad \text{[Equation 3]}$$

In the light entering into the phase image generator 610, unnecessary elements are removed through the first and second filtering. Since obtaining the phase delay of the light in pixel-wise manner is possible, it is practicable to make an image using the quantitative phase delay information of the target sample.

Although only a few embodiments of the present invention have been shown and described, the present invention is not limited to the described embodiments. Instead, as would be appreciated by those skilled in the art, changes may be made to these embodiments without departing from the principles of the invention, the scope of which is defined by the claims and their equivalents.

What is claimed is:

1. A method of measuring a relative phase of a bio-cell using a digital image sensor, the method comprising the steps of:
    firstly filtering a light emitted from a light source, using a first polarizer and a first wave plate, which are arranged in order on an optical path;
    exposing a bio-cell to the firstly filtered light;
    secondly filtering the light passing through the bio-cell, using a second wave plate and a second polarizer, which are arranged in order on the optical path; and
    sensing an intensity of the secondly filtered light, by each of pixels of an image sensor,
    wherein, as conditions of the second filtering are varied, optical properties of the bio-cell are calculated using the intensity of the light in a pixel-wise manner,
    wherein the first wave plate and the second wave plate are provided by using a quarter-wavelength plate,
    wherein the first wave plate and the second wave plate are positioned at 45° and 135° respectively to a polarization axis defined by the first polarizer, and
    wherein a Jones matrix of the optical properties calculated in a pixel-wise manner is as follows:

$$\begin{bmatrix} E_x \\ E_y \end{bmatrix} = \begin{bmatrix} \cos\beta & -\sin\beta \\ \sin\beta & \cos\beta \end{bmatrix} \begin{bmatrix} 1 & 0 \\ 0 & 0 \end{bmatrix} \begin{bmatrix} \cos\beta & \sin\beta \\ -\sin\beta & \cos\beta \end{bmatrix} \begin{bmatrix} \cos(135°) & -\sin(135°) \\ \sin(135°) & \cos(135°) \end{bmatrix}$$

$$\begin{bmatrix} e^{i\frac{\pi}{4}} & 0 \\ 0 & e^{-i\frac{\pi}{4}} \end{bmatrix} \begin{bmatrix} \cos(135°) & \sin(135°) \\ -\sin(135°) & \cos(135°) \end{bmatrix} \times \begin{bmatrix} e^{i\frac{\delta}{2}} & 0 \\ 0 & e^{i\frac{\delta}{2}} \end{bmatrix} \begin{bmatrix} \cos 45 & -\sin 45 \\ \sin 45 & \cos 45 \end{bmatrix}$$

$$\begin{bmatrix} e^{i\frac{\pi}{4}} & 0 \\ 0 & e^{-i\frac{\pi}{4}} \end{bmatrix} \begin{bmatrix} \cos 45 & \sin 45 \\ -\sin 45 & \cos 45 \end{bmatrix} \begin{bmatrix} 0 \\ 1 \end{bmatrix} E_0 e^{i\omega t}$$

whereby $E_x$ and $E_y$ are intensities of the light respectively to x axis and y axis, $\beta$ is a rotating angle of the second polarizer, $\delta$ is a phase delay by the bio-cell, $E_0$ is an amplitude of an initial light, $\omega$ is a frequency of the initial light.

2. The method of claim 1, wherein the conditions of the second filtering are varied by varying the polarization angle of the second polarizer.

3. The method of claim 2, wherein the polarization angle is varied by $\pi/4$.

4. The method of claim 1, wherein a specific wave-length of light selected from the light emitted from the light source is used for the first filtering.

5. An apparatus of measuring a relative phase of a bio-cell comprising:
    a light source member having a light source emitting light;
    a first polarizer for polarizing the light from the light source to a specific direction of polarization state;
    a first wave plate for affecting the polarization direction of the light passing through the first polarizer;
    a stage plate for locating the bio-cell on an optical path of the light passing through the first wave plate;
    a second wave plate for affecting the polarization direction of the light passing though the stage plate;
    a second polarizer for polarizing the light passing through the second wave plate to another specific direction of polarization state; and
    an image reading member having an image sensor detecting intensities of the light passing through the second polarizer,
    wherein the first wave plate and the second wave plate are provided by using a quarter-wave length plate,
    wherein the first wave plate and the second wave plate are positioned at 45° and 135° respectively to a polarization axis defined by the first polarizer, and
    wherein a Jones matrix of the optical properties calculated in a pixel-wise manner is as follows:

$$\begin{bmatrix} E_x \\ E_y \end{bmatrix} = \begin{bmatrix} \cos\beta & -\sin\beta \\ \sin\beta & \cos\beta \end{bmatrix} \begin{bmatrix} 1 & 0 \\ 0 & 0 \end{bmatrix} \begin{bmatrix} \cos\beta & \sin\beta \\ -\sin\beta & \cos\beta \end{bmatrix} \begin{bmatrix} \cos(135°) & -\sin(135°) \\ \sin(135°) & \cos(135°) \end{bmatrix}$$

$$\begin{bmatrix} e^{i\frac{\pi}{4}} & 0 \\ 0 & e^{-i\frac{\pi}{4}} \end{bmatrix} \begin{bmatrix} \cos(135°) & \sin(135°) \\ -\sin(135°) & \cos(135°) \end{bmatrix} \times \begin{bmatrix} e^{i\frac{\delta}{2}} & 0 \\ 0 & e^{i\frac{\delta}{2}} \end{bmatrix} \begin{bmatrix} \cos 45 & -\sin 45 \\ \sin 45 & \cos 45 \end{bmatrix}$$

$$\begin{bmatrix} e^{i\frac{\pi}{4}} & 0 \\ 0 & e^{-i\frac{\pi}{4}} \end{bmatrix} \begin{bmatrix} \cos 45 & \sin 45 \\ -\sin 45 & \cos 45 \end{bmatrix} \begin{bmatrix} 0 \\ 1 \end{bmatrix} E_0 e^{i\omega t}$$

whereby $E_x$ and $E_y$ are intensities of the light respectively to x axis and y axis, $\beta$ is a rotating angle of the second polarizer, $\delta$ is a phase delay by the bio-cell, $E_0$ is an amplitude of an initial light, $\omega$ is a frequency of the initial light.

6. The apparatus of claim 5, wherein the second polarizer comprises a linear polarizer, which varies the polarization state by rotating by $\lambda/4$.

7. The apparatus of claim 5, wherein the second polarizer comprises a polarizing rotator having a liquid-crystal phase delayer, such that the polarization state is varied according to the liquid-crystal state of the liquid-crystal phase delayer.

8. The apparatus of claim 5, wherein the light source member further has a band pass filter for passing a specific wavelength of light selected from the light emitted from the light source.

* * * * *